(12) United States Patent
Tao et al.

(10) Patent No.: US 10,786,386 B2
(45) Date of Patent: Sep. 29, 2020

(54) MEDICAL BODY POSITION RETAINING BELT SECURING DEVICE

(71) Applicant: MAQUET (SUZHOU) CO. LTD., Suzhou (CN)

(72) Inventors: Xiaowang Tao, Suzhou (CN); Wei Peng, Suzhou (CN); Qingxue Li, Suzhou (CN); Hongqiang Li, Suzhou (CN); Ming Ji, Suzhou (CN)

(73) Assignee: Maquet (Suzhou) Co., Ltd., Suzhou (CN)

( * ) Notice: Subject to any disclaimer, the term of this patent is extended or adjusted under 35 U.S.C. 154(b) by 728 days.

(21) Appl. No.: 15/029,668

(22) PCT Filed: Sep. 15, 2014

(86) PCT No.: PCT/CN2014/086487
§ 371 (c)(1),
(2) Date: Apr. 15, 2016

(87) PCT Pub. No.: WO2015/055064
PCT Pub. Date: Apr. 23, 2015

(65) Prior Publication Data
US 2016/0235579 A1    Aug. 18, 2016

(30) Foreign Application Priority Data
Oct. 18, 2013    (CN) .......................... 2013 1 0495302

(51) Int. Cl.
*A61F 5/37* (2006.01)
*A61G 13/10* (2006.01)

(52) U.S. Cl.
CPC .............. *A61F 5/3776* (2013.01); *A61F 5/37* (2013.01); *A61G 13/10* (2013.01); *A61G 13/101* (2013.01)

(58) Field of Classification Search
CPC .. A61G 13/101; A61G 2203/78; A61G 13/10; A61F 5/3769; A61F 5/3776;
(Continued)

(56) References Cited

U.S. PATENT DOCUMENTS

| 5,433,222 A | 7/1995 | Boomgaarden |
| 6,622,980 B2 | 9/2003 | Boucher et al. |
| 2013/0019883 A1 | 1/2013 | Worm et al. |

FOREIGN PATENT DOCUMENTS

| CN | 103126847 | 6/2013 |
| CN | 103300992 A * | 9/2013 |

(Continued)

OTHER PUBLICATIONS

Office Action (including English translation) issued in corresponding Japanese Office Action, dated Mar. 6, 2017, 10 pages.
(Continued)

*Primary Examiner* — Rachael E Bredefeld
*Assistant Examiner* — Caitlin A Carreiro
(74) *Attorney, Agent, or Firm* — Quarles & Brady LLP

(57) ABSTRACT

A medical body position retaining belt securing device is disclosed. The medical body position retaining belt securing device for securing and releasing a medical body position retaining belt to and from an operating table side guide rail, comprising an upper clamping piece, a lower clamping piece and an elastic piece, the upper clamping piece or the lower clamping piece being coupled to the medical body position retaining belt, each of the upper clamping piece and the lower clamping piece including a clamping portion for clamping the operating table side guide rail, and two ends of the elastic piece respectively abutting against or being secured to the upper clamping piece and the lower clamping piece.

24 Claims, 10 Drawing Sheets

(58) Field of Classification Search
CPC .. A61F 5/37; F16B 2200/40; F16B 2200/403; B25B 5/04; B25B 1/04
USPC ........... 128/869, 876; 403/257, 385; 24/455, 24/457; 248/229.23, 229.24; 5/621
See application file for complete search history.

(56) References Cited

FOREIGN PATENT DOCUMENTS

| | | |
|---|---|---|
| CN | 103300992 A | 9/2013 |
| CN | 103315872 A | 9/2013 |
| CN | 103315874 A | 9/2013 |
| CN | 103536421 A | 1/2014 |
| CN | 203591416 U | 5/2014 |
| DE | 202007009094 U1 | 11/2007 |
| DE | 102009021222 A1 | 11/2010 |
| JP | 2015-140166 | 6/2005 |
| JP | 2005140166 A | 6/2005 |
| KR | 20110005517 A | 1/2011 |

OTHER PUBLICATIONS

European Patent Office, Communication Pursuant to Article 94(3) EPC, corresponding European Application No. 14 854 744.1, dated Jun. 11, 2018, 5 pages.
Supplementary European Search Report issued in corresponding European Patent Application No. 1484744.1, dated Jun. 13, 2017, 8 pages.
PCT International Search Report, PCT/CN2014/086487, dated Nov. 28, 2014.
Intellectual Property Office of Singapore, Search Report, Application No. 11201603020U, dated Oct. 27, 2016.
Intellectual Property Office of Singapore, Written Opinion, Application No. 11201603020U, dated Nov. 3, 2016.
Japan Patent Office, Notice of Reasons for Rejection, Application No. 2016-524458, dated Oct. 2, 2017, 10 pages.

* cited by examiner

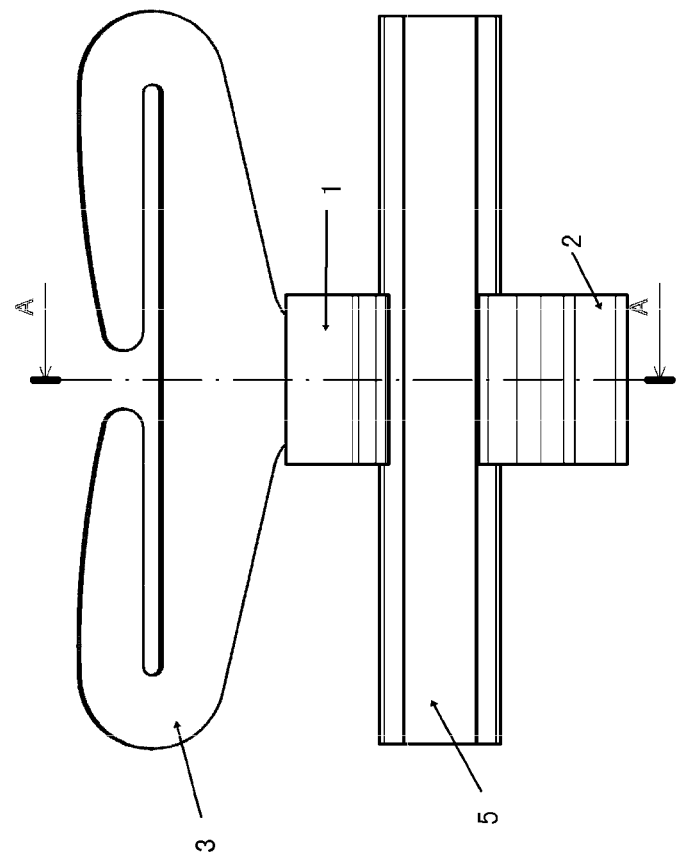
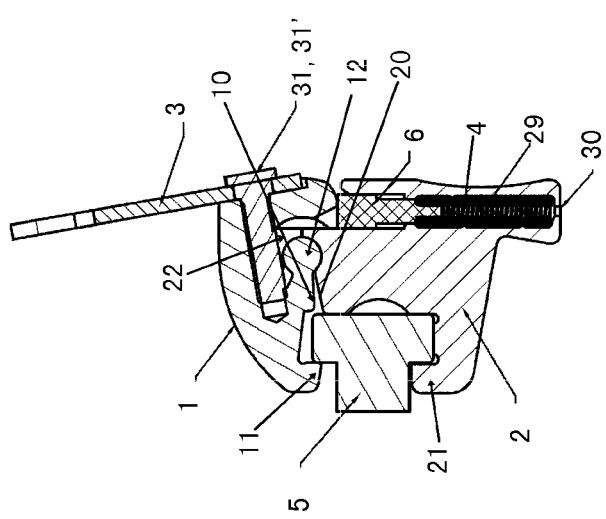

MEDICAL BODY POSITION RETAINING BELT SECURING DEVICE

CROSS-REFERENCE TO RELATED APPLICATIONS

The present application represents to the US National Stage of International Application PCT/CN2014/086487 filed Sep. 15, 2014, which claims priority to Chinese Patent Application 201310495302.6 filed on Oct. 18, 2013, which is incorporated herein by reference in its entirety.

TECHNICAL FIELD

The present invention relates to a medical body position retaining belt securing device, in particular to a medical body position retaining belt securing device used for securing and releasing a medical body position retaining belt to and from an operating table side guide rail.

BACKGROUND ART

At present, in the medical field, when a patient needs to have an operation, a hospital usually uses a tying-type belt (also referred as a "medical body position retaining belt") to restrain body parts of a patient to prevent the patient from causing an injury to himself during movement. Usually, one end or both ends of the existing medical body position retaining belt is installed with a securing device, and the medical body position retaining belt is secured to a side guide rail of an operating table through the securing device so as to keep the body position of the patient unchanged.

The existing medical body position retaining belt securing device mainly adopts two solutions: one solution is to adopt a sheet metal bent structure (for example, as shown in FIG. 1(a)) which realizes gravity self-locking by virtue of an oscillating block 100 after being combined with a side guide rail 105, i.e., separation cannot be realized under the situation that the oscillating block is not lifted up; and the other solution is to realize securing by virtue of bolts.

Defects of solution one: since there is no pre-tightening force and it can freely slide after being combined with the side guide rail, it can only be installed between side guide rail connecting columns 106 and cannot be installed at a position with an opening at one end (as shown in FIG. 1(b)); in addition, when the side guide rail and a horizontal plane form an angle of 30°, the sheet metal bent structure will slide; and due to the structural peculiarity thereof, the medical body position retaining belt securing device of solution one cannot adapt to side guide rails of different operating tables.

Defects of solution two: adopting bolts 200 to realize locking and securing (as shown in FIG. 2) is not only time-consuming, but also not easy to clean.

SUMMARY OF THE INVENTION

An object of the present invention is to overcome the above-mentioned defects of the existing medical body position retaining belt securing devices and provide a medical body position retaining belt securing device which can provide a pre-clamping force, can be installed at any position on an operating table side guide rail to ensure that the device does not slide when the side guide rail and a horizontal plane form an angle of 30°, can be used for side guide rails of different operating tables (as long as there is a certain height of the side guide rail), avoids the use of bolts for securing so as to improve the use efficiency and be easily cleaned.

The above-mentioned object of the present invention is realized through a medical body position retaining belt securing device. The medical body position retaining belt securing device is used for securing and releasing a medical body position retaining belt to and from an operating table side guide rail, wherein the medical body position retaining belt securing device comprises an upper clamping piece, a lower clamping piece and an elastic piece, the upper clamping piece or the lower clamping piece being coupled to the medical body position retaining belt, the upper clamping piece and the lower clamping piece being respectively provided with a clamping portion for clamping the operating table side guide rail, and two ends of the elastic piece respectively abutting against or being secured to the upper clamping piece and the lower clamping piece, and the medical body position retaining belt securing device can present a clamping state and an open state, wherein in the clamping state, the elastic piece moves the clamping portion of the upper clamping piece and the clamping portion of the lower clamping piece towards each other by virtue of an elastic force thereof, such that the medical body position retaining belt is secured to the operating table side guide rail, while in the open state, the elastic force of the elastic piece is overcome to move the clamping portion of the upper clamping piece and the clamping portion of the lower clamping piece away from each other, so as to release the medical body position retaining belt from the operating table side guide rail.

According to the above-mentioned technical solution, the medical body position retaining belt securing device of the present invention can provide the following beneficial technical effects: the medical body position retaining belt securing device can provide a pre-clamping force, can be installed at any position on an operating table side guide rail to ensure that the device does not slide when the side guide rail and a horizontal plane form an angle of 30°, can be used for side guide rails of different operating tables (as long as there is a certain height of the side guide rail), avoids the use of bolts for securing so as to improve the use efficiency and be easily cleaned.

Preferably, the upper clamping piece or the lower clamping piece is coupled to the medical body position retaining belt through a retaining belt coupling piece, one end of the retaining belt coupling piece being secured to the medical body position retaining belt and the other end of the retaining belt coupling piece being secured to the upper clamping piece or the lower clamping piece.

According to the above-mentioned technical solution, the medical body position retaining belt securing device of the present invention can provide the following beneficial technical effect: by adopting the additional retaining belt coupling piece, the coupling between the medical body position retaining belt and the medical body position retaining belt securing device is made more firm.

Preferably, the elastic piece is arranged within an elastic piece containing portion of at least one clamping piece of the upper clamping piece and the lower clamping piece.

According to the above-mentioned technical solution, the medical body position retaining belt securing device of the present invention can provide the following beneficial technical effects: by arranging the elastic piece containing portion within at least one clamping piece of the upper clamping piece and the lower clamping piece and arranging the elastic piece within the elastic piece containing portion, the installation of the elastic piece is made more simple and convenient, and the elastic piece is concealed during use so as to prevent contamination to medical personnel.

Preferably, the upper clamping piece and the lower clamping piece can pivot relative to each other about a pivot.

According to the above-mentioned technical solution, the medical body position retaining belt securing device of the present invention can provide the following beneficial technical effect: it can be more convenient to switch between the clamping state and the open state, so as to facilitate securing and releasing the medical body position retaining belt to and from the operating table side guide rail.

Preferably, the pivot is integrally formed on the upper clamping piece or the lower clamping piece.

According to the above-mentioned technical solution, the medical body position retaining belt securing device of the present invention can provide the following beneficial technical effects: the structure of the medical body position retaining belt securing device is simplified and the number of component is decreased.

Preferably, the lower clamping piece or the upper clamping piece is provided with a slot, and a limiting piece is arranged within the slot to prevent the upper clamping piece and the lower clamping piece from transversely moving relative to each other.

According to the above-mentioned technical solution, the medical body position retaining belt securing device of the present invention can provide the following beneficial technical effect: the upper clamping piece and the lower clamping piece can be effectively prevented from transversely moving relative to each other, such that the medical body position retaining belt securing device does not easily fall apart.

Preferably, the pivot is separately formed and passes through the upper clamping piece and the lower clamping piece.

According to the above-mentioned technical solution, the medical body position retaining belt securing device of the present invention can provide the following beneficial technical effect: it can be more convenient to switch between the clamping state and the open state, so as to facilitate securing and releasing the medical body position retaining belt to and from the operating table side guide rail.

Preferably, one end of the pivot is provided with a pivot cap, and the other end of the pivot is connected with a securing screw to prevent the upper clamping piece and the lower clamping piece from transversely moving relative to each other.

According to the above-mentioned technical solution, the medical body position retaining belt securing device of the present invention can provide the following beneficial technical effect: the upper clamping piece and the lower clamping piece can be effectively prevented from transversely moving relative to each other, such that the medical body position retaining belt securing device does not easily fall apart.

Preferably, the elastic piece is a compression spring.

According to the above-mentioned technical solution, the medical body position retaining belt securing device of the present invention can provide the following beneficial technical effect: it can be more convenient to switch between the clamping state and the open state, so as to facilitate securing and releasing the medical body position retaining belt to and from the operating table side guide rail.

Preferably, one end of the elastic piece abuts against a bottom surface of the elastic piece containing portion of at least one clamping piece and the other end of the elastic piece abuts against the at least other clamping piece of the upper clamping piece and the lower clamping piece.

According to the above-mentioned technical solution, the medical body position retaining belt securing device of the present invention can provide the following beneficial technical effects: it can be more convenient to switch between the clamping state and the open state and the installation of the elastic piece is relatively stable, such that the medical body position retaining belt securing device does not easily fall apart.

Preferably, the medical body position retaining belt securing device further comprises a sliding block inserted between the elastic piece and the at least other clamping piece of the upper clamping piece and the lower clamping piece and partially contained within the elastic piece containing portion.

According to the above-mentioned technical solution, the medical body position retaining belt securing device of the present invention can provide the following beneficial technical effects: the sliding block is usually made of wear-resistant materials (such as plastic) so as to avoid excessive wear between the elastic piece and the upper clamping piece; and a contact area of the sliding block and the upper clamping piece is usually larger than direct contact area of the elastic piece and the upper clamping piece, so as to ensure more stable contact between the elastic piece and the upper clamping piece and make the entire medical body position retaining belt securing device more firm.

Preferably, the elastic piece is a tension spring, a torsion spring or a leaf spring.

According to the above-mentioned technical solution, the medical body position retaining belt securing device of the present invention can provide the following beneficial technical effects: various types of elastic pieces can be adopted to enable the medical body position retaining belt securing device to be conveniently switched between the clamping state and the open state, so as to facilitate securing and releasing the medical body position retaining belt to and from the operating table side guide rail.

Preferably, the upper clamping piece and the lower clamping piece are extrusion-formed.

According to the above-mentioned technical solution, the medical body position retaining belt securing device of the present invention can provide the following beneficial technical effects: even though the shapes and constructions of the upper clamping piece and the lower clamping piece are complex, for example, rotating shafts, rotating shaft surrounding portions, clamping portions, abutting portions, elastic piece containing portions and the like are formed, the upper clamping piece and the lower clamping piece can be simply extrusion-formed, wherein the manufacturing time is short and the mass production can be realized. For example, long sections of the clamping pieces can be firstly extrusion-formed and then are cut into a plurality of clamping pieces, which greatly improves the clamping piece production efficiency.

Preferably, at least one clamping piece provided with the elastic piece containing portion in the upper clamping piece and the lower clamping piece is provided with a ventilation hole at one end thereof, the ventilation hole being communicated with the elastic piece containing portion to facilitate the action of the elastic piece.

According to the above-mentioned technical solution, the medical body position retaining belt securing device of the present invention can provide the following beneficial technical effects: for example, in the case of the compression spring, since the medical body position retaining belt securing device is repetitively opened and clamped, the compression spring is repetitively compressed and restored, thus air is inevitably pressed into the elastic piece containing portion such that a certain air pressure is caused to be present within the elastic piece containing portion, and the air pressure will obstruct the normal operation by the user to the medical body position retaining belt securing device, for example, opening of the medical body position retaining belt securing device by the user; however, by arranging the ventilation hole in communication with the elastic piece containing portion, excessive air can be exhausted, such that the user can conveniently operate (especially open) the medical body position retaining belt securing device.

Preferably, the medical body position retaining belt securing device can further present a pre-use state in which an abutting portion of the upper clamping piece and an abutting portion of the lower clamping piece abut against each other by virtue of the elastic force of the elastic piece.

According to the above-mentioned technical solution, the medical body position retaining belt securing device of the present invention can provide the following beneficial technical effects: the clamping portion of the upper clamping piece and the clamping portion of the lower clamping piece can be prevented from getting too close during the pre-use state due to the elastic force of the elastic piece so as to avoid a too large elastic force needed to be overcome by the user upon switching the medical body position retaining belt securing device from the pre-use state to the opened state, such that clamping of the medical body position retaining belt securing device can be more simple and easy; and when the medical body position retaining belt securing device is not used, the medical body position retaining belt securing device can be stably kept in the pre-use state, such that the medical body position retaining belt securing device does not easily fall apart.

Preferably, the other end of the retaining belt coupling piece is secured onto the upper clamping piece by virtue of a screw rod.

According to the above-mentioned technical solution, the medical body position retaining belt securing device of the present invention can provide the following beneficial technical effect: it can be conveniently and adjustably secure the retaining belt coupling piece to the upper clamping piece.

Preferably, the other end of the retaining belt coupling piece is secured to the upper clamping piece by virtue of a screw rod and the screw rod forms the limiting piece.

According to the above-mentioned technical solution, the medical body position retaining belt securing device of the present invention can provide the following beneficial technical effects: the screw rod can simultaneously have two functions, wherein one function is to adjustably secure the other end of the retaining belt coupling piece to the upper clamping piece, and the other function is to prevent the upper clamping piece and the lower clamping piece from transversely moving relative to each other. Thus the number of the components of the medical body position retaining belt securing device can be decreased and the design can be simplified.

Preferably, the upper clamping piece is provided with an arc-shaped step portion on a surface of the upper clamping piece secured with the retaining belt coupling piece, so as to realize a maximum deflection angle of 30° of the retaining belt coupling piece.

According to the above-mentioned technical solution, the medical body position retaining belt securing device of the present invention can provide the following beneficial technical effects: the maximum deflection angle of the retaining belt coupling piece is limited to be 30° so as to avoid compromising the safety of the patient during operation due to lateral sliding.

Preferably, the lower clamping piece or the upper clamping piece is provided with a lug portion, so as to facilitate grasping by a user in use.

According to the above-mentioned technical solution, the medical body position retaining belt securing device of the present invention can provide the following beneficial technical effect: when the user secures the medical body position retaining belt to the operating table side guide rail or adjusts the position of the medical body position retaining belt, the opening and the clamping of the medical body position retaining belt securing device can be realized by a single hand, such that the securing or adjusting process of the medical body position retaining belt is simpler and quicker.

Preferably, the clamping portion is a hook-shaped clamping portion.

According to the above-mentioned technical solution, the medical body position retaining belt securing device of the present invention can provide the following beneficial technical effect: the operating table side guide rail can be more stably and reliably clamped.

Preferably, the shape of the upper clamping piece is designed in such a manner that an additional clamping force applied by the hook-shaped clamping portion of the upper clamping piece to the operating table side guide rail is multiply increased as an additional tensioning force of the medical body position retaining belt is increased.

According to the above-mentioned technical solution, the medical body position retaining belt securing device of the present invention can provide the following beneficial technical effects: regardless of unconscious actions of the patient during operation, the patient can be firmly retained at a certain position; the more fierce the action of the patient is (i.e., the larger the additional tensioning force of the medical body position retaining belt is), the larger the additional clamping force applied by the hook-shaped clamping portion of the upper clamping piece to the operating table side guide rail is, and thus the patient is firmly retained at a certain position; and the additional clamping force applied by the hook-shaped clamping portion of the upper clamping piece to the operating table side guide rail can multiply magnify the additional tensioning force of the medical body position retaining belt, wherein the magnification time is $L1/L2$, so as to ensure that the patient is firmly retained at a certain position.

Preferably, the medical body position retaining belt securing device further comprises a gasket arranged between the retaining belt coupling piece and the upper clamping piece or the lower clamping piece.

According to the above-mentioned technical solution, the medical body position retaining belt securing device of the present invention can provide the following beneficial technical effects: the retaining belt coupling piece is spaced from the upper clamping piece or the lower clamping piece, so as to avoid mutual friction between the retaining belt coupling piece and the upper clamping piece or the lower clamping piece in the use of the medical body position retaining belt securing device; and absolute linkage between the retaining belt coupling piece and the upper clamping piece or the lower clamping piece is prevented and further rightward oscillation of the retaining belt coupling piece will drive the upper clamping piece or the lower clamping piece to be opened only upon the retaining belt coupling piece rightwards oscillating to a rightmost limit position, such that the medical body position retaining belt securing device of the present invention is safer.

Preferably, the medical body position retaining belt securing device further comprises a sliding block, one end of the elastic piece abuts against or is secured to at least one clamping piece of the upper clamping piece and the lower clamping piece, and the other end of the elastic piece abuts against or is secured to the at least other clamping piece of the upper clamping piece and the lower clamping piece by virtue of the sliding block.

According to the above-mentioned technical solution, the medical body position retaining belt securing device of the present invention can provide the following beneficial technical effects: the sliding block is usually made of wear-resistant materials (such as plastic) so as to avoid excess wear between the elastic piece and the upper clamping piece/lower clamping piece; and contact area between the sliding block and the upper clamping piece/lower clamping piece is usually larger than direct contact area between the elastic piece and the upper clamping piece/lower clamping piece, so as to ensure a more stable contact between the elastic piece and the upper clamping piece/lower clamping piece and make the entire medical body position retaining belt securing device firmer.

Preferably, the elastic piece and the sliding block are both arranged along a horizontal direction.

Preferably, the elastic piece and the sliding block are both arranged along a vertical direction.

According to the above-mentioned technical solution, the medical body position retaining belt securing device of the present invention can provide the following beneficial technical effect: the elastic piece and the sliding block can be flexibly arranged along different directions according to different requirements.

Preferably, the sliding block is provided with an elastic piece containing portion and the elastic piece is at least partially contained within the elastic piece containing portion.

According to the above-mentioned technical solution, the medical body position retaining belt securing device of the present invention can provide the following beneficial technical effects: the installation of the elastic piece can be made simpler and more convenient, and the elastic piece is concealed during use so as to prevent contamination to medical personnel.

BRIEF DESCRIPTION OF THE DRAWINGS

FIG. 4 illustrates a front view of a medical body position retaining belt securing device in a clamping state according to one embodiment of the present invention.

FIG. 5 illustrates a sectional view along a centerline A-A of FIG. 4 of a medical body position retaining belt securing device in a clamping state according to one embodiment of the present invention.

FIG. 7 illustrates side views of a medical body position retaining belt securing device respectively in a pre-use state, an open state and a clamping state according to one embodiment of the present invention, wherein FIG. 7(a) illustrates the pre-use state, FIG. 7(b) illustrates the open state and FIG. 7(c) illustrates the clamping state.

Figure 1A:
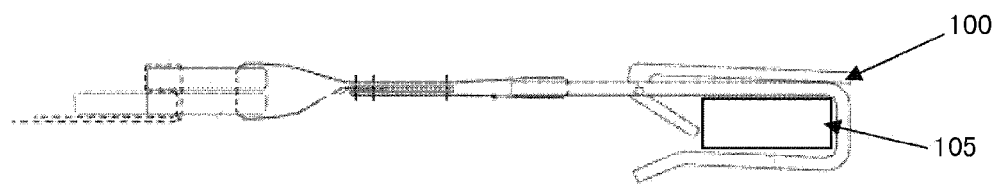
FIG. 1(a) illustrates a side view of a medical body position retaining belt securing device in a sheet metal bent structure in the prior art.
Figure 1B:
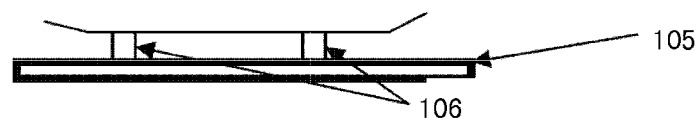
FIG. 1(b) illustrates a schematic view of a part of an operating table and a side guide rail thereof.
Figure 2:
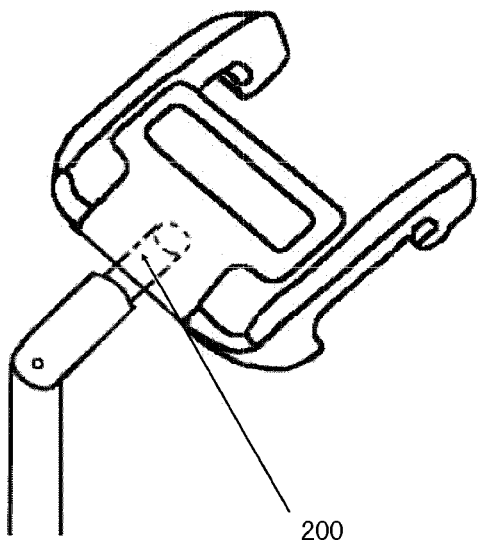
FIG. 2 illustrates a side view of another medical body position retaining belt securing device in the prior art, which realizes securing by virtue of bolts.

In the drawings: 1-upper clamping piece; 2-lower clamping piece; 3-retaining belt coupling piece; 4-elastic piece, 4'-elastic piece; 5-operating table side guide rail; 6-sliding block; 6'-sliding block; 10-abutting portion; 11-clamping portion; 12-pivot; 12'-pivot; 12"-pivot cap; 13-step portion; 20-abutting portion; 21-clamping portion; 22-pivot surrounding portion; 29-elastic piece containing portion; 29'-elastic piece containing portion; 31-limiting piece; 31'-screw rod; 32-gasket; 100-oscillating block; 105-operating table side guide rail; 106-side guide rail connecting column; 200-bolt.

DETAILED DESCRIPTION

The preferred embodiments of the present invention will be described below in combination with the drawings.

Figure 3:
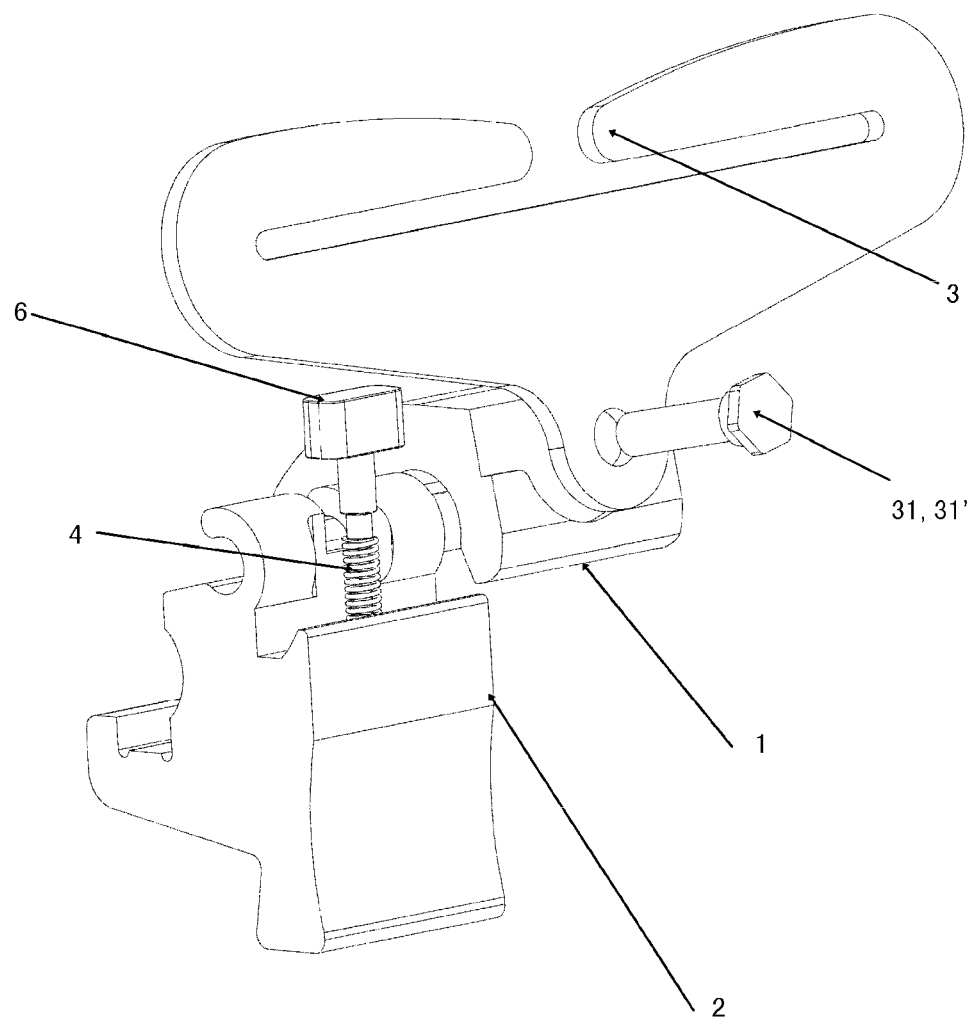
FIG. 3 illustrates an exploded assembly view of a medical body position retaining belt securing device according to one embodiment of the present invention.

FIG. 3 illustrates an exploded assembly view of a medical body position retaining belt securing device according to one embodiment of the present invention. The medical body position retaining belt securing device according to one embodiment of the present invention is used for securing and releasing a medical body position retaining belt to and from an operating table side guide rail. The medical body position retaining belt securing device comprises an upper clamping piece 1, a lower clamping piece 2 and an elastic piece 4, the upper clamping piece 1 or the lower clamping piece 2 being coupled to the medical body position retaining belt. The two ends of the elastic piece 4 respectively abut against or are secured to the upper clamping piece 1 and the lower clamping piece 2.

The upper clamping piece 1 or the lower clamping piece 2 can be directly coupled to the medical body position retaining belt. Of course, the upper clamping piece 1 or the lower clamping piece 2 can also be coupled to the medical body position retaining belt by virtue of the retaining belt coupling piece 3, wherein one end of the retaining belt coupling piece 3 is secured to the medical body position retaining belt and the other end of the retaining belt coupling piece 3 is secured to the upper clamping piece 1 or the lower clamping piece 2 (for example, FIG. 3 illustrates that the other end of the retaining belt coupling piece 3 is secured to the upper clamping piece 1).

Preferably, the elastic piece 4 is arranged within an elastic piece containing portion 29 of at least one clamping piece of the upper clamping piece 1 and the lower clamping piece 2.

Figure 6:
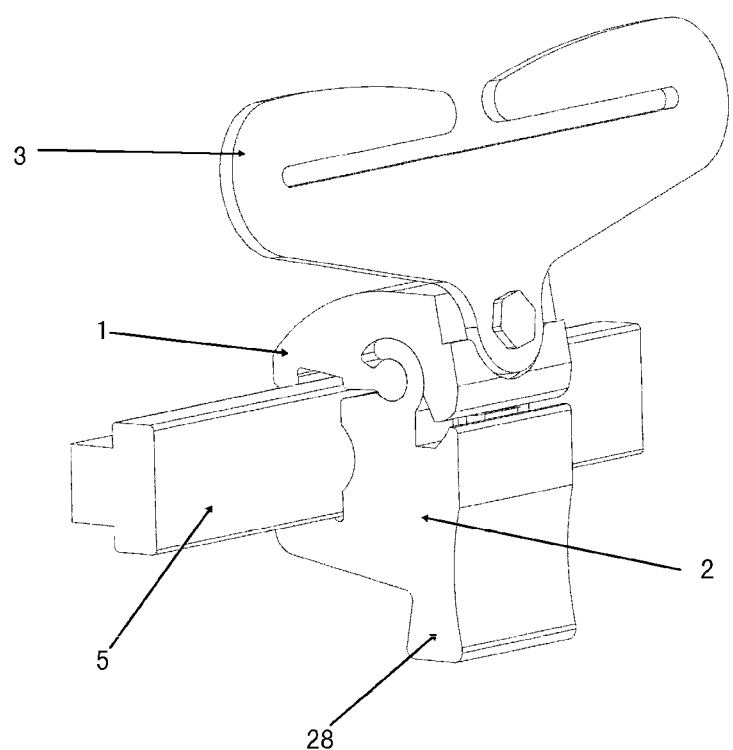
FIG. 6 illustrates a stereoscopic view of a medical body position retaining belt securing device in a clamping state according to one embodiment of the present invention.

FIG. 4 illustrates a front view of a medical body position retaining belt securing device in a clamping state according to one embodiment of the present invention. FIG. 5 illustrates a sectional view along a centerline A-A of FIG. 4 of a medical body position retaining belt securing device in a clamping state according to one embodiment of the present invention. FIG. 6 illustrates a stereoscopic view of a medical body position retaining belt securing device in a clamping state according to one embodiment of the present invention.

As shown in FIG. 5, the upper clamping piece 1 and the lower clamping piece 2 are respectively provided with clamping portions 11 and 21 for clamping the operating table side guide rail 5.

Although FIG. 5 only illustrates that the elastic piece 4 is arranged within the elastic piece containing portion 29 of the lower clamping piece 2, on the basis of the present invention, one skilled in the art can understand that the elastic piece 4 can also be arranged within the elastic piece containing portion of the upper clamping piece 1.

As shown in FIG. 5, the clamping portions 11 and 21 are preferably hook-shaped clamping portions. Of course, the clamping portions 11 and 21 can also be in other shapes, as long as the operating table side guide rail 5 can be reliably clamped. For example, the clamping portions 11 and 21 can be planar clamping portions which are substantially in flush with other portions of the clamping pieces.

In the clamping state as shown in FIGS. 4-6, the elastic piece 4 moves the clamping portion (the clamping portion 11 as shown in FIGS. 4-6) of the other clamping piece (the upper clamping piece 1 as shown in FIGS. 4-6) of the upper clamping piece and the lower clamping piece towards the clamping portion (the clamping portion 21 as shown in FIGS. 4-6) of one clamping piece (the lower clamping piece 2 as shown in FIGS. 4-6) by virtue of an elastic force of the elastic piece, so as to secure the medical body position retaining belt onto the operating table side guide rail 5.

Figure 7:
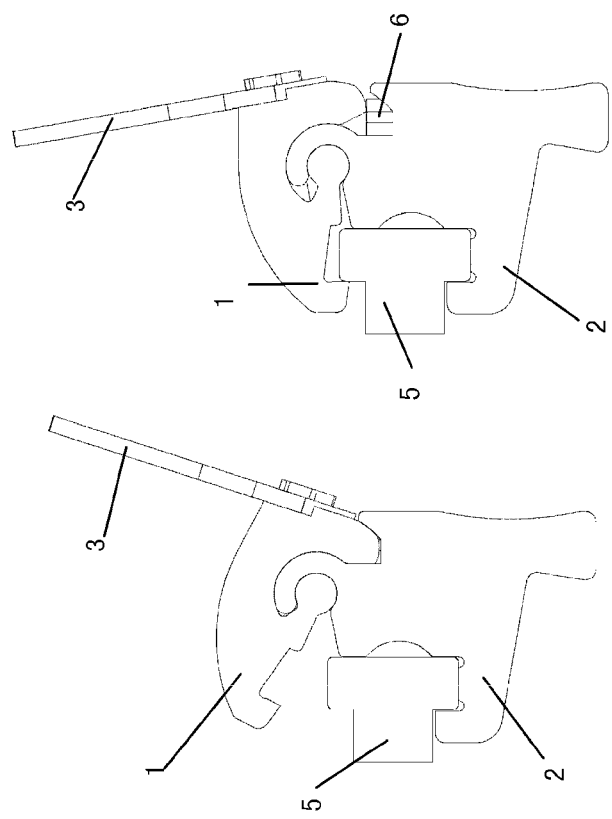

FIG. 7 illustrates side views of a medical body position retaining belt securing device respectively in a pre-use state, an open state and a clamping state according to one embodiment of the present invention, wherein FIG. 7(a) illustrates the pre-use state, FIG. 7(b) illustrates the open state and FIG. 7(c) illustrates the clamping state.

In the clamping state as shown in FIG. 7(c), as described above, the elastic piece 4 moves the clamping portion 11 of the upper clamping piece 1 towards the clamping portion 21 of the lower clamping piece by virtue of the elastic force of the elastic piece, so as to secure the medical body position retaining belt onto the operating table side guide rail 5.

In the open state as shown in FIG. 7(b), the elastic force of the elastic piece 4 is overcome to move the clamping portion 11 of the upper clamping piece 1 away from the clamping portion 21 of the lower clamping piece 2, so as to release the medical body position retaining belt from the operating table side guide rail 5 and to facilitate securing the medical body position retaining belt onto the operating table side guide rail 5 again after release.

Preferably, the upper clamping piece 1 and the lower clamping piece 2 can also be respectively provided with an abutting portion 10 and an abutting portion 20.

In the pre-use state as shown in FIG. 7(a), the abutting portion 10 of the upper clamping piece 1 and the abutting portion 20 of the lower clamping piece 2 abut against each other by virtue of the elastic force of the elastic piece 4. Since the abutting portion 10 of the upper clamping piece 1 and the abutting portion 20 of the lower clamping piece 2 abut against each other in the pre-use state, the following beneficial technical effects can be realized: the clamping portion 11 of the upper clamping piece 1 and the clamping portion 21 of the lower clamping piece 2 can be prevented from getting too close due to the elastic force of the elastic piece 4 in the pre-use state so as to further avoid a too large elastic force needed to be overcome by the user upon switching the medical body position retaining belt securing device from the pre-use state to the opened state, such that the clamping of the medical body position retaining belt securing device is more simple and easy; and when the medical body position retaining belt securing device is not used, the medical body position retaining belt securing device can be stably kept in the pre-use state, such that the medical body position retaining belt securing device does not easily fall apart.

Of course, the abutting portion 10 of the upper clamping piece 1 and the abutting portion 20 of the lower clamping piece 2 may also be not additionally arranged, and by directly abutting the clamping portion 11 of the upper clamping piece 1 and the clamping portion 21 of the lower clamping piece 2 in the pre-use state, the technical effect of stably retaining the medical body position retaining belt securing device in the pre-use state can also be realized, and such medical body position retaining belt securing device can also effectively secure the medical body position retaining belt onto the operating table side guide rail. Under this situation, compared with the situation of additionally arranging the abutting portion 10 of the upper clamping piece 1 and the abutting portion 20 of the lower clamping piece, the user needs to overcome a larger elastic force upon switching the medical body position retaining belt securing device from the pre-use state to the open state.

Although FIGS. 4-7 only illustrate that the elastic piece 4 moves the clamping portion 11 of the upper clamping piece 1 towards the clamping portion 21 of the lower clamping piece 2, on the basis of the present invention, one skilled in the art can understand that the elastic piece 4 can also move the clamping portion 21 of the lower clamping piece towards the clamping portion 11 of the upper clamping piece 1 when the elastic piece 4 is arranged within the elastic piece containing portion of the upper clamping piece.

The upper clamping piece 1 and the lower clamping piece 2 can pivot relative to each other about a pivot 12.

In one embodiment, as shown in FIG. 5, the pivot 12 is integrally formed on the upper clamping piece 1 and a pivot surrounding portion 22 is arranged on the lower clamping piece 2. Of course, on the basis of the present invention, one skilled in the art can understand that the pivot can also be integrally formed on the lower clamping piece 2, the pivot surrounding portion can also be arranged on the upper clamping piece 1, and the technical effect that the upper clamping piece 1 and the lower clamping piece 2 pivot relative to each other around the pivot can also be realized.

Under the situation that the pivot 12 is integrally formed on the upper clamping piece 1 as shown in FIG. 5, the lower clamping piece 2 is provided with a slot. Preferably, the slot can be arranged at a transverse middle position of the pivot surrounding portion 22 of the lower clamping piece as shown in FIG. 3. As shown in FIG. 5, a limiting piece 31 is arranged within the slot to prevent the upper clamping piece 1 and the lower clamping piece 2 from transversely moving relative to each other.

Figure 8:
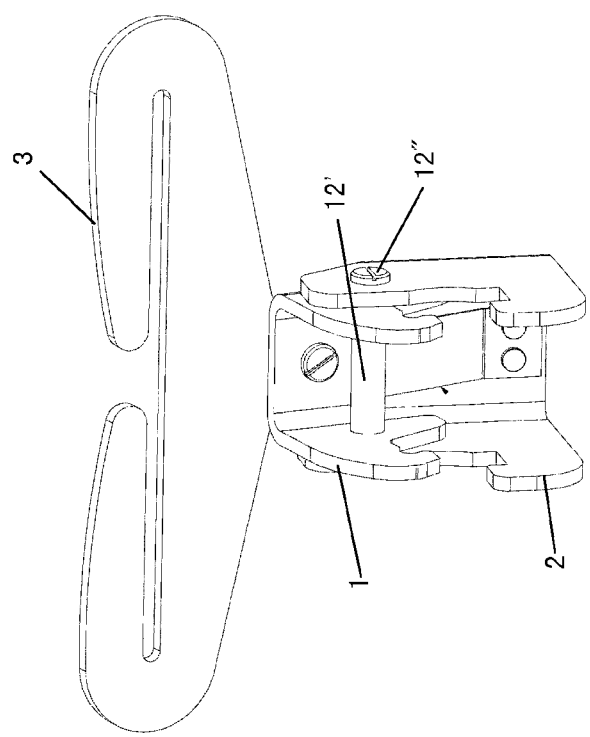
FIG. 8 illustrates a stereoscopic view of a medical body position retaining belt securing device according to another embodiment of the present invention.

In another embodiment, as shown in FIG. 8, a pivot 12' is separately formed and passes through the upper clamping piece 1 and the lower clamping piece 2. One end of the pivot 12' is provided with a pivot cap 12", and the other end of the pivot 12' is connected with a securing screw (not shown) to prevent the upper clamping piece 1 and the lower clamping piece 2 from transversely moving relative to each other.

Although the technical solution that the upper clamping piece 1 and the lower clamping piece 2 can pivot relative to each other around the pivot 12 is described above, on the basis of the present invention, one skilled in the art can understand that the upper clamping piece 1 and the lower clamping piece 2 can also adopt other connection solutions to realize the clamping state and the open state of the medical body position retaining belt securing device. For example, the upper clamping piece 1 and the lower clamping piece 2 can be connected by adopting a sliding rail, wherein in the clamping state, the elastic piece moves the clamping portion of the upper clamping piece 1 or the lower clamping piece 2 towards the clamping portion of the lower clamping piece 2 or the upper clamping piece 1 by virtue of the elastic force of the elastic piece, so as to secure the medical body position retaining belt onto the operating table side guide rail, and in the open state, the elastic force of the elastic piece is overcome to move the clamping portion of the upper clamping piece 1 or the lower clamping piece 2 away from the clamping piece of the lower clamping piece 2 or the upper clamping piece 1, so as to release the medical body position retaining belt from the operating table side guide rail.

The elastic piece 4 is preferably a compression spring, as shown in FIG. 5. One end of the compression spring 4 abuts against a bottom surface of the elastic piece containing portion 29 of the lower clamping piece 2 and the other end of the compression spring 4 abuts against the upper clamping piece 1. Of course, the other end of the compression spring 4 can also not directly abut against the upper clamping piece 1 but instead abut against the upper clamping piece 1 by virtue of a sliding block 6.

Specifically, the medical body position retaining belt securing device according to one embodiment of the present invention can further comprise a sliding block 6, as shown in FIG. 5, the sliding block 6 is inserted between the elastic piece 4 and the upper clamping piece 1 and is partially contained within the elastic piece containing portion 29. Inserting the sliding block 6 between the elastic piece 4 and the upper clamping piece 1 has the following beneficial technical effects: the sliding block is usually made of wear-resistant materials (such as plastic) so as to avoid excess wear between the elastic piece 4 and the upper clamping piece 1; and the contact area between the sliding block and the upper clamping piece is usually larger than direct contact area between the elastic piece and the upper clamping piece so as to ensure a more stable contact between the elastic piece and the upper clamping piece and make the entire medical body position retaining belt securing device firmer.

Although the elastic piece 4 is the compression spring in the embodiment as shown in FIG. 5, on the basis of the present invention, one skilled in the art can understand that the elastic piece 4 can also be a tension spring, a torsion spring or a leaf spring, and even other types of springs or elastic pieces which can realize the clamping state and the open state of the medical body position retaining belt securing device.

Under the situation that the elastic piece 4 is the tension spring, the two ends of the tension spring are respectively secured to the upper clamping piece 1 and the lower clamping piece 2, so as to pull the respective clamping portions of the upper clamping piece 1 and the lower clamping piece 2 towards each other by virtue of the tension force of the tension spring in the clamping state and overcome the tension force of the tension spring in the open state to enable the respective clamping portions of the upper clamping piece 1 and the lower clamping piece 2 to move away from each other.

Under the situation that the elastic piece 4 is the torsion spring, the two ends of the torsion spring are respectively secured to the upper clamping piece 1 and the lower clamping piece 2, so as to move the respective clamping portions of the upper clamping piece 1 and the lower clamping piece 2 towards each other by virtue of the torsion force of the torsion spring in the clamping state and overcome the torsion force of the torsion spring in the open state to enable the respective clamping portions of the upper clamping piece 1 and the lower clamping piece 2 to move away from each other.

Under the situation that the elastic piece 4 is the leaf spring (as shown in FIG. 8), one end of the leaf spring is secured to the lower clamping piece 2 and the other end of the leaf spring abuts against the upper clamping piece 1, so as to move the respective clamping portions of the upper clamping piece 1 and the lower clamping piece 2 towards each other by virtue of the elastic force of the leaf spring in the clamping state and overcome the elastic force of the leaf spring in the open state to enable the respective clamping portions of the upper clamping piece 1 and the lower clamping piece 2 to move away from each other.

Preferably, the upper clamping piece 1 and the lower clamping piece 2 are extrusion-formed. That is, the upper clamping piece 1 and the lower clamping piece 2 can be in the form of clamping blocks. The extrusion-formed upper clamping piece and lower clamping piece have the following beneficial technical effects: even though the shapes and constructions of the upper clamping piece and the lower clamping piece are complex, for example, rotating shafts, rotating shaft surrounding portions, clamping portions, abutting portions, elastic piece containing portions and the like are formed, the upper clamping piece and the lower clamping piece can also be simply extrusion-formed, the manufacturing time is short and the mass production can be realized. For example, long sections of the clamping pieces can be firstly extrusion-formed, and then the long sections of the clamping pieces are cut into a plurality of clamping pieces, which greatly improves the clamping piece production efficiency.

Of course, on the basis of the present invention, one skilled in the art can understand that the upper clamping piece 1 and the lower clamping piece 2 can also adopt other forming methods, for example, sheet metal bending forming and the like. However, such forming method cannot realize the above-mentioned beneficial technical effects brought by extrusion forming.

Preferably, one clamping piece (for example, the lower clamping piece 2 as shown in FIG. 5) provided with the elastic piece containing portion 29 of the lower clamping piece 2 and the upper clamping piece 1 is provided with a ventilation hole 30 at one end thereof, and the ventilation hole 30 is communicated with the elastic piece containing portion 29 to facilitate the action of the elastic piece 4. The arrangement of the above-mentioned ventilation hole has the following beneficial technical effects: for example, under the situation of the compression spring as shown in FIG. 5, since the medical body position retaining belt securing device is repetitively opened and clamped, the compression spring is repetitively compressed and restored, thus air is inevitably pressed into the elastic piece containing portion and a certain air pressure is caused to be present within the elastic piece containing portion, such an air pressure will obstruct the normal operation by the user to the medical body position retaining belt securing device, for example, obstruct the opening of the medical body position retaining belt securing device by the user; however, by arranging the ventilation hole communicated with the elastic piece containing portion, excess air can be exhausted, such that the user can conveniently operate (especially open) the medical body position retaining belt securing device.

Preferably, the other end of the retaining belt coupling piece 3 is secured to the upper clamping piece 1 by virtue of a screw rod 31', as shown in FIG. 5. Thus, the deflection angle of the retaining belt coupling piece can be conveniently adjusted, so as to further conveniently adjust the restraining position and angle of the medical body position retaining belt.

Preferably, the screw rod 31' forms the above-mentioned limiting piece 31. Thus, the screw rod 31' can simultaneously have two functions: one function is to adjustably secure the other end of the retaining belt coupling piece 3 to the upper clamping piece 1, and the other function is to prevent the upper clamping piece 1 and the lower clamping piece 2 from transversely moving relative to each other. Thus, the number of the components of the medical body position retaining belt securing device can be reduced and the design can be simplified.

Figure 9:
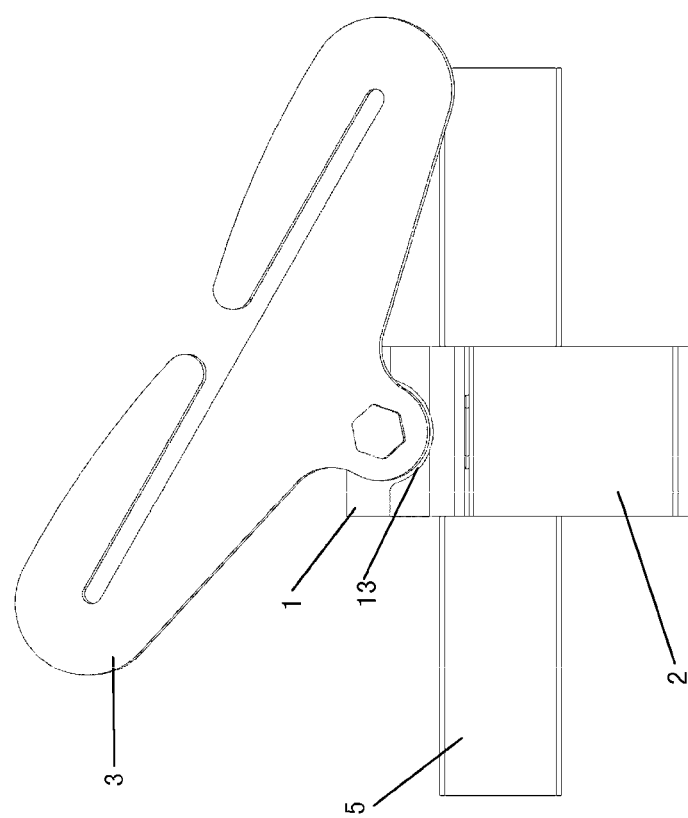
FIG. 9(a) illustrates a working state view of a retaining belt coupling piece at a maximum leftward deflection angle.
FIG. 9(b) illustrates a working state view of a retaining belt coupling piece at a maximum rightward deflection angle.
Figure 9:
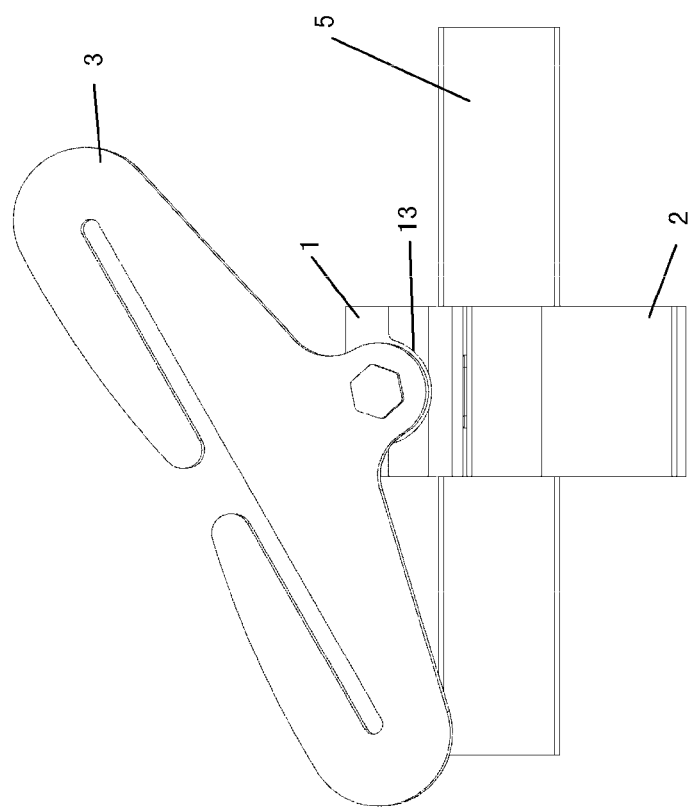

As shown in FIG. 9(a) and FIG. 9(b), the upper clamping piece 1 is provided with an arc-shaped step portion 13 on a surface of the upper clamping piece 1 secured with the retaining belt coupling piece 3, so as to realize a maximum deflection angle of 30° of the retaining belt coupling piece 3. FIG. 9(a) illustrates that a maximum leftward deflection angle of the retaining belt coupling piece 3 is 30°. FIG. 9(b) illustrates that a maximum rightward deflection angle of the retaining belt coupling piece 3 is 30°. Of course, in order to fit with the arc-shaped step portion 13 of the upper clamping piece 1, a corresponding end surface of the retaining belt coupling piece 3 is also designed to be arc-shaped, as shown in FIG. 9(a) and FIG. 9(b).

The inventor finds that, if the maximum deflection angle of the retaining belt coupling piece 3 exceeds 30°, the entire medical body position retaining belt securing device easily side laterally, such that the safety of the patient may be jeopardized during operation. Therefore, as described above, the arc-shaped step portion 13 of the upper clamping piece 1 is designed to limit the maximum deflection angle of the retaining belt coupling piece 3 to be 30°.

Preferably, the lower clamping piece 2 or the upper clamping piece 1 is provided with a lug portion 28, so as to facilitate grasping by a user in use. For example, referring to FIG. 6, the lower clamping piece 2 is provided with a lug portion 28. Thus, when the user secures the medical body position retaining belt to the operating table side guide rail or adjusts the position of the medical body position retaining belt, the opening and the clamping of the medical body position retaining belt securing device can be realized by a single hand, such that the securing or adjusting process of the medical body position retaining belt is simpler and quicker.

Figure 10:
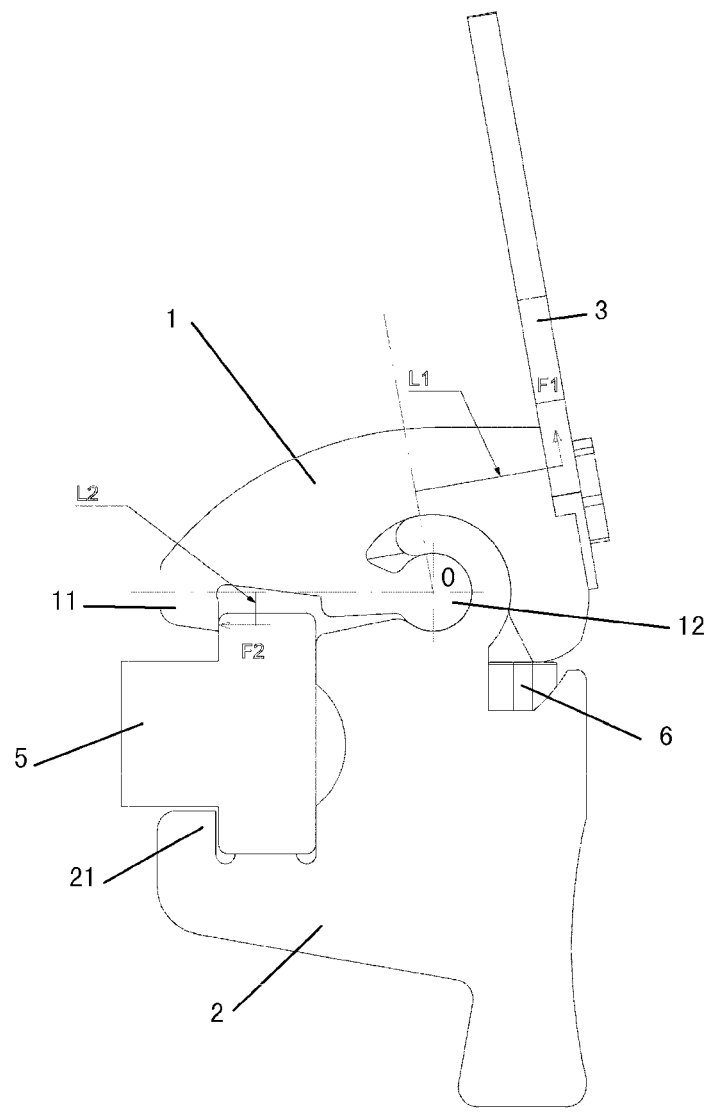
FIG. 10 illustrates a mechanical principle view of a medical body position retaining belt securing device according to one embodiment of the present invention.

FIG. 10 illustrates a mechanical principle view of a medical body position retaining belt securing device according to one embodiment of the present invention. When the medical body position retaining belt securing device is secured in position and the patient quietly lies on the operating table, the additional tensioning force of the medical body position retaining belt is zero, i.e., the additional force F1 applied by the medical body position retaining belt to the upper clamping piece 1 by virtue of the retaining belt coupling piece 3 is zero. Once there is an additional tensioning force (for example, from an unconscious action of the patient) acting on the medical body position retaining belt, the hook-shaped clamping portion 11 of the upper clamping piece of the medical body position retaining belt securing device will have an additional clamping force applied onto the operating table side guide rail, and at this moment, the upper clamping piece 1 will be subjected to a counter-acting force F2 which comes from the operating table side guide rail and is equal in magnitude but opposite in direction from the additional clamping force. As shown in FIG. 10, a fulcrum of the pivot 12 is O, force arms of force F1 and force F2 are respectively L1 and L2, and a following relationship exists: F1*L1=F2*L2. Also as shown in FIG. 10, since force arm L1 is several times of force arm L2, force F2 is several times of force F1. Therefore, an additional clamping force applied by the hook-shaped clamping portion of the upper clamping piece to the operating table side guide rail is multiply increased as an additional tensioning force of the medical body position retaining belt is increased. The above-mentioned design (mainly the shape design of the upper clamping piece) of the medical body position retaining belt securing device has the following beneficial technical effects: regardless of unconscious actions of the patient during operation, the patient can be firmly retained at a certain position; the more fierce the action of the patient is (i.e., the larger the additional tensioning force of the medical body position retaining belt is), the larger the additional clamping force applied by the hook-shaped clamping portion of the upper clamping piece to the operating table side guide rail is, so as to ensure that the patient is firmly retained at a certain position; and the additional clamping force applied by the hook-shaped clamping portion of the upper clamping piece to the operating table side guide rail can multiply magnify the additional tensioning force of the medical body position retaining belt, wherein the magnification time is L1/L2, so as to further endure that the patient is firmly retained at a certain position.

Figure 11:
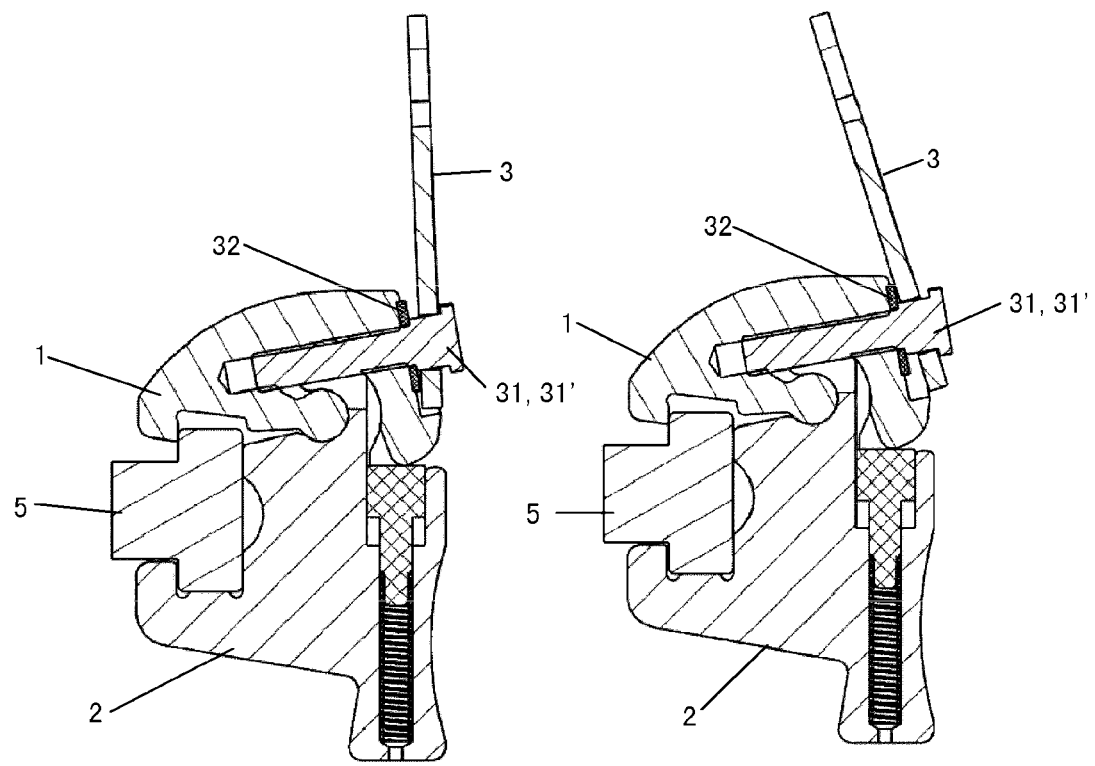
FIG. 11(a) and FIG. 11(b) illustrate a sectional view of a medical body position retaining belt securing device according to another embodiment of the present invention.

FIG. 11(a) and FIG. 11(b) illustrate a sectional view of a medical body position retaining belt securing device according to another embodiment of the present invention. Compared with the embodiment as shown in FIG. 5, the embodiments as shown in FIG. 11(a) and FIG. 11(b) arrange a gasket 32 between the retaining belt coupling piece 3 and the upper clamping piece 1, and the gasket 32 is used for spacing the retaining belt coupling piece 3 from the upper clamping piece 1 to avoid mutual friction between the retaining belt coupling piece 3 and the upper clamping piece 1 in the use of the medical body position retaining belt securing device. The gasket 32 is preferably a plastic gasket. Of course, the gasket 32 can also be made of other wear-resistant materials.

Besides, as shown in FIG. 11(a) and FIG. 11(b), since the gasket 32 is arranged between the retaining belt coupling piece 3 and the upper clamping piece 1, the retaining belt coupling piece 3 obtains a degree of freedom of leftward and right oscillations within a certain range. FIG. 11(a) illustrates a state when the retaining belt coupling piece 3 oscillates to a rightmost limit position, and FIG. 11(b) illustrates a state when the retaining belt coupling piece 3 oscillates to a leftmost limit position. Thus, absolute linkage between the retaining belt coupling piece 3 and the upper clamping piece 1 is avoided and further rightward oscillation of the retaining belt coupling piece 3 will drive the opening of the upper clamping piece 1 only upon the retaining belt coupling piece 3 rightwards oscillating to the rightmost limit position, such that the medical body position retaining belt securing device of the present invention is safer.

Preferably, the gasket 32 is at least partially embedded into a groove in the upper clamping piece 1, such that the arrangement of the gasket 32 is firmer.

Although the embodiments a shown in FIG. 11(a) and FIG. 11(b) only illustrate the situation that the retaining belt coupling piece 3 is secured to the upper clamping piece 1, on the basis of the present invention, one skilled in the art can understood that, under the situation that the retaining belt coupling piece 3 is secured to the lower clamping piece 2, the gasket 32 can also be arranged between the retaining belt coupling piece 3 and the lower clamping piece 2.

Figure 12:
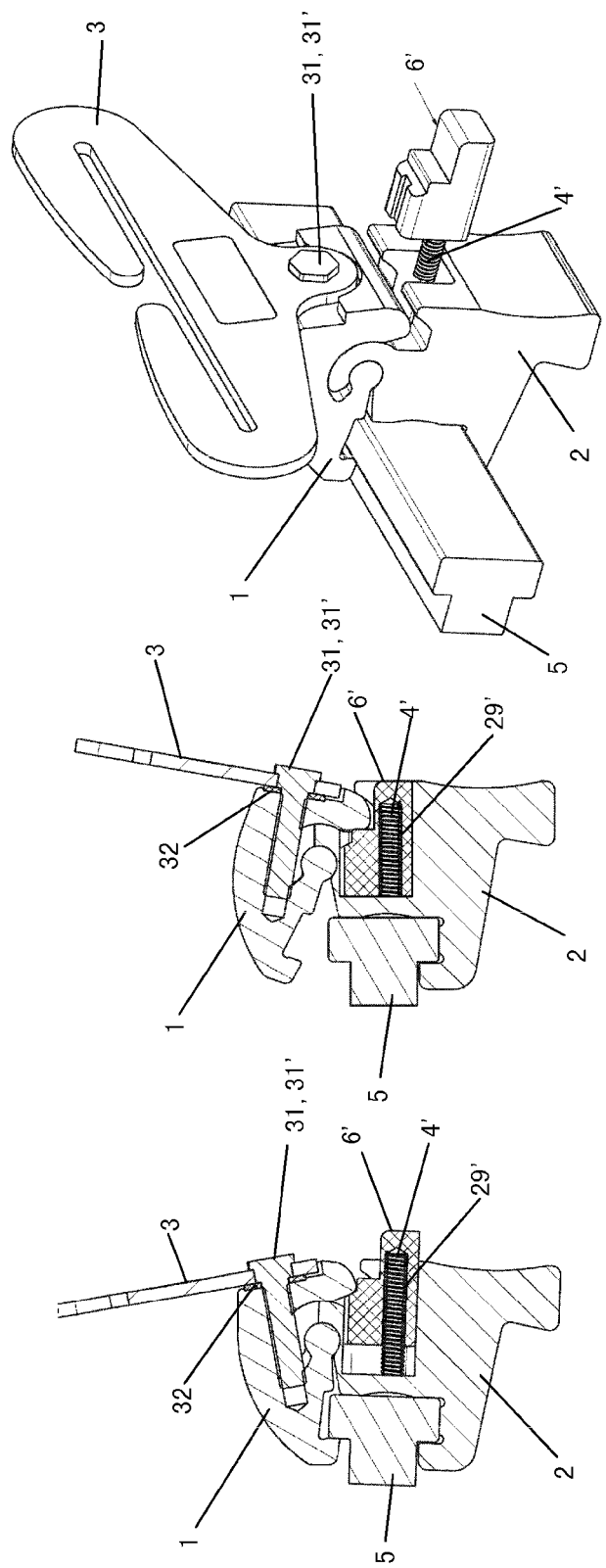
FIG. 12(a) illustrates a sectional view of a medical body position retaining belt securing device in a clamping state according to another embodiment of the present invention.
FIG. 12(b) illustrates a sectional view of a medical body position retaining belt securing device in an open state according to another embodiment of the present invention and FIG. 12(c) illustrates an exploded assembly view of a medical body position retaining belt securing device according to another embodiment of the present invention.

FIGS. 12(a)-12(c) illustrate a clamping state sectional view, an open state sectional view and an exploded assembly view of a medical body position retaining belt securing device according to another embodiment of the present invention.

As shown in FIGS. 12(a)-12(c), the medical body position retaining belt securing device comprises a sliding block 6', one end of the elastic piece 4' abuts against or is secured to the lower clamping piece 2, and other end of the elastic piece 4' abuts against or is secured to the upper clamping piece 1 by virtue of the sliding block 6'.

The distinction of the embodiments as shown in FIGS. 12(a)-12(c) and the embodiments as shown in FIG. 11(a) and FIG. 11(b) lies in that: in the embodiments as shown in FIGS. 12(a)-12(c), the elastic piece 4' and the sliding block 6' are both arranged along a horizontal direction, while in the embodiments as shown in FIG. 11(a) and FIG. 11(b), the elastic piece 4 and the sliding block 6 are both arranged along a vertical direction.

Preferably, the sliding block 6' is provided with an elastic piece containing portion 29', and the elastic piece 4' is at least partially contained within the elastic piece containing portion 29'.

Although the embodiments as shown in FIGS. 12(a)-12(b) only illustrate the situation that the elastic piece 4' and the sliding block 6' are both located in the lower clamping piece 2, on the basis of the present invention, one skilled in the art can understand that the elastic piece 4' and the sliding block 6' can also be located in the upper clamping piece 1.

The present invention is exemplarily described above in combination with the drawings. Obviously, the specific implementation of the present invention is not limited by the above-mentioned embodiments. One skilled in the art can make various modifications or variations to the present invention without departing from the technical concept of the present invention. Such modifications or variations certainly also fall into the protection range of the present invention.

The invention claimed is:

1. A medical body position retaining belt securing device, which is used for securing and releasing a medical body position retaining belt to and from an operating table side guide rail, characterized in that the medical body position retaining belt securing device comprises an upper clamping piece, a lower clamping piece and an elastic piece having two ends, the upper clamping piece or the lower clamping piece being coupled to the medical body position retaining belt, each of the upper clamping piece and the lower clamping piece including a clamping portion for clamping the operating table side guide rail, and two ends of the elastic piece respectively abutting against or being secured to the upper clamping piece and the lower clamping piece, and the medical body position retaining belt securing device can present a clamping state and an open state, wherein in the clamping state, the elastic piece moves the clamping portion of the upper clamping piece and the clamping portion of the lower clamping piece towards each other by virtue of an elastic force thereof, such that the medical body position retaining belt is secured to the operating table side guide rail, while in the open state, the elastic force of the elastic piece is overcome to move the clamping portion of the upper clamping piece and the clamping portion of the lower clamping piece away from each other, so as to release the medical body position retaining belt from the operating table side guide rail, wherein the upper clamping piece or the lower clamping piece is coupled to the medical body position retaining belt through a retaining belt coupling piece including two ends, one end of the retaining belt coupling piece being secured to the medical body position retaining belt and the other end of the retaining belt coupling piece being secured to the upper clamping piece or the lower clamping piece, wherein the upper clamping piece is provided with an arc-shaped step portion on a surface of the upper clamping piece so that a peripheral edge of the retaining belt coupling piece is shaped to cooperate with a peripheral edge of the arc-shaped step portion to realize a maximum deflection angle of 30° of the retaining belt coupling piece relative to the upper clamping piece, wherein the medical body position retaining belt securing device can further present a pre-use state in which an abutting portion of the upper clamping piece and an abutting portion of the lower clamping piece abut against each other by virtue of the elastic force of the elastic piece, and wherein the upper clamping piece and the lower clamping piece can pivot relative to each other about a pivot, the abutting portion of the upper clamping piece is located near the pivot, the clamping portion of the upper clamping piece is located away from the pivot, the abutting portion of the lower clamping piece is located near the pivot, the clamping portion of the lower clamping piece is located away from the pivot.

2. The medical body position retaining belt securing device according to claim 1, wherein the pivot is integrally formed on the upper clamping piece or the lower clamping piece.

3. The medical body position retaining belt securing device according to claim 2, wherein the lower clamping piece or the upper clamping piece is provided with a slot, and a limiting piece is arranged within the slot to prevent the upper clamping piece and the lower clamping piece from transversely moving relative to each other.

4. The medical body position retaining belt securing device according to claim 3, wherein the other end of the retaining belt coupling piece is secured to the upper clamping piece by virtue of a screw rod and the screw rod forms the limiting piece.

5. The medical body position retaining belt securing device according to claim 1, wherein the elastic piece is arranged within an elastic piece containing portion of at least one clamping piece of the upper clamping piece and the lower clamping piece.

6. The medical body position retaining belt securing device according to claim 5, wherein the elastic piece includes two ends, and one end of the elastic piece abuts against a bottom surface of the elastic piece containing portion of at least one clamping piece and the other end of the elastic piece abuts against at least another clamping piece of the upper clamping piece and the lower clamping piece.

7. The medical body position retaining belt securing device according to claim 5, wherein the medical body position retaining belt securing device further comprises a sliding block inserted between the elastic piece and at least another clamping piece of the upper clamping piece and the lower clamping piece and partially contained within the elastic piece containing portion.

8. The medical body position retaining belt securing device according to claim 5, wherein at least one clamping piece provided with the elastic piece containing portion in the upper clamping piece and the lower clamping piece is provided with a ventilation hole at one end thereof, the ventilation hole being communicated with the elastic piece containing portion to facilitate the action of the elastic piece.

9. The medical body position retaining belt securing device according to claim 1, wherein the medical body position retaining belt securing device further comprises a sliding block, one end of the elastic piece abutting against or being secured to at least one clamping piece of the upper clamping piece and the lower clamping piece, and the other end of the elastic piece abutting against or being secured to at least another clamping piece of the upper clamping piece and the lower clamping piece by virtue of the sliding block.

10. The medical body position retaining belt securing device according to claim 9, wherein the elastic piece and the sliding block are both arranged along a horizontal direction.

11. The medical body position retaining belt securing device according to claim 9, wherein the elastic piece and the sliding block are both arranged along a vertical direction.

12. The medical body position retaining belt securing device according to claim 9, wherein the sliding block is provided with an elastic piece containing portion and the elastic piece is at least partially contained within the elastic piece containing portion.

13. The medical body position retaining belt securing device according to claim 1, wherein the pivot is separately formed and passes through the upper clamping piece and the lower clamping piece.

14. The medical body position retaining belt securing device according to claim 13, wherein one end of the pivot is provided with a pivot cap, and the other end of the pivot is connected with a securing screw to prevent the upper clamping piece and the lower clamping piece from transversely moving relative to each other.

15. The medical body position retaining belt securing device according to claim 1, wherein the clamping portion is a hook-shaped clamping portion.

16. The medical body position retaining belt securing device according to claim 15, wherein a shape of the upper clamping piece is designed in such a manner that an additional clamping force applied by the hook-shaped clamping portion of the upper clamping piece to the operating table side guide rail is multiply increased as an additional tensioning force of the medical body position retaining belt is increased.

17. The medical body position retaining belt securing device according to claim 1, wherein the elastic piece is a compression spring.

18. The medical body position retaining belt securing device according to claim 1, wherein the elastic piece is a tension spring, a torsion spring or a leaf spring.

19. The medical body position retaining belt securing device according to claim 1, wherein the upper clamping piece and the lower clamping piece are extrusion-formed.

20. The medical body position retaining belt securing device according to claim 1, wherein the other end of the retaining belt coupling piece is secured to the upper clamping piece by virtue of a screw rod.

21. The medical body position retaining belt securing device according to claim 1, wherein the lower clamping piece or the upper clamping piece is provided with a lug portion, so as to facilitate grasping by a user in use.

22. The medical body position retaining belt securing device according to claim 1, wherein the medical body position retaining belt securing device further comprises a gasket arranged between the retaining belt coupling piece and the upper clamping piece or the lower clamping piece.

23. The medical body position retaining belt securing device according to claim 1, wherein, in the pre-use state, the clamping portion of the upper clamping piece is prevented from contacting the clamping portion of the lower clamping piece.

24. The medical body position retaining belt securing device according to claim 1, wherein, in the clamping state, the abutting portion of the upper clamping piece is separated from the abutting portion of the lower clamping piece.

* * * * *